US009012649B2

(12) United States Patent
Mashima et al.

(10) Patent No.: US 9,012,649 B2
(45) Date of Patent: Apr. 21, 2015

(54) METHOD FOR PRODUCING OPTICALLY ACTIVE 2-ARYLPIPERIDINIUM SALT

(71) Applicant: Takasago International Corporation, Ota-ku, Tokyo (JP)

(72) Inventors: Kazushi Mashima, Ikeda (JP); Yusuke Kita, Minoo (JP); Takuto Nagano, Osaka (JP); Atsuhiro Iimuro, Ikeda (JP); Kenta Yamaji, Gifu (JP); Shoji Hida, Konan (JP); Kiyoto Hori, Koza-gun (JP); Hideki Nara, Fujisawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 14/168,101

(22) Filed: Jan. 30, 2014

(65) Prior Publication Data
US 2014/0213792 A1 Jul. 31, 2014

(30) Foreign Application Priority Data

Jan. 31, 2013 (JP) ................................. 2013-017337

(51) Int. Cl.
*C07D 211/02* (2006.01)
*C07D 213/26* (2006.01)
*C07B 53/00* (2006.01)
*C07D 211/12* (2006.01)

(52) U.S. Cl.
CPC .............. *C07D 213/26* (2013.01); *C07B 53/00* (2013.01); *C07D 211/12* (2013.01)

(58) Field of Classification Search
CPC .................................................. C07D 211/02
USPC ........................................................ 546/185
See application file for complete search history.

(56) References Cited

U.S. PATENT DOCUMENTS

| 4,990,517 | A | 2/1991 | Petersen et al. |
| 5,059,597 | A | 10/1991 | Petersen et al. |
| 5,416,096 | A | 5/1995 | Petersen et al. |
| 5,607,942 | A | 3/1997 | Petersen et al. |
| 2009/0036696 | A1 | 2/2009 | Mashima et al. |

FOREIGN PATENT DOCUMENTS

| EP | 0 350 733 B1 | 8/1997 |
| JP | 07-242630 A | 9/1995 |
| WO | 2006/022020 A1 | 3/2006 |

OTHER PUBLICATIONS

Wang et al. Chemical Reviews, 2012, 12, 2557-2590.*
Wang et al. Journal of Organic Chemistry (2009), 74(7), 2780-2787.*
Dorwald F. A. Side Reactions in Organic Synthesis, 2005, Wiley: VCH, Weinheim p. IX of Preface p. 1-15.*
Augustine, Robert. "Chapter 17—Hydrogenation IV: Aromatic Compounds" Heterogeneous Catalysis for the Synthetic Chemist, 1996, pp. 421-424.
European Patent Office, Extended European Search Report dated Mar. 18, 2014, issued in counterpart European Application No. 14 15 2648.3.
Yusuke Kita et al., "Iridium-Catalzed Asymmetric Hydrogenation of Pyridinium Salts for Constructing Multiple Stereogenic Centers on Piperidines," Chemistry Letters, The Chemical Society of Japan, 2014.
Guangrong Zheng et al., "Synthesis and evaluation of a series of homologues of lobelane at the vesicular monoamine transporter-2", Bioorganic & Medicinal Chemistry Letters, vol. 18, No. 24, 2008, pp. 6509-6512.
Atsuhiro Iimuro et al., "Asymmetric Hydrogenation of Isoquinolinium Salts Catalyzed by Chiral Iridium Complexes: Direct Synthesis for Optically Active 1,2,3,4-Tetrahydroisoquinolines," Angewandte Chemie International Edition, vol. 52, No. 7, 2013, pp. 2046-2050.

(Continued)

Primary Examiner — Nizal Chandrakumar
(74) Attorney, Agent, or Firm — Sughrue Mion, PLLC

(57) ABSTRACT

Disclosed is a method for producing an optically active 2-arylpiperidinium salt, comprising asymmetrically hydrogenating a pyridinium salt in the presence of an iridium complex and hydrogen, the 2-arylpiperidinium salt being represented by the following general formula (1):

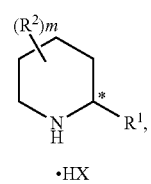

(1)

wherein $R^1$, $R^2$, X, *, and m are as described in Description, the pyridinium salt being represented by the following general formula (2):

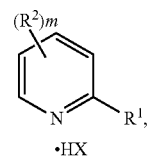

(2)

wherein $R^1$, $R^2$, X, and m are as described in Description, and the iridium complex being represented by the following general formula (3):

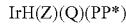

$$IrH(Z)(Q)(PP^*) \qquad (3),$$

wherein Z, PP*, and Q are as described in Description, or the following general formula (4):

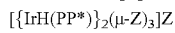

$$[\{IrH(PP^*)\}_2(\mu\text{-}Z)_3]Z \qquad (4),$$

wherein Z and PP* are as described in Description.

5 Claims, No Drawings

(56) References Cited

OTHER PUBLICATIONS

Xiao-Bing Wang et al., "Iridium-catalyzed asymmetric hydrogenation of pyridine derivatives, 7, 8-dihydro-quinolin-5(6H)-ones", Tetrahedron Letters, vol. 49, No. 33, 2008, pp. 4922-4924.

Duo-Sheng Wang et al., "Asymmetric Hydrogenation of Heteroarenes and Arenes", Chemical Reviews, vol. 112, No. 4, 2012, pp. 2557-2590.

"Heterogeneous Catalysis for the Synthetic Chemist", 1996, Chapter 17, pp. 421-424.

Duo-Sheng Wang et al., "Asymmetric Hydrogenation of Heteroarenes and Arenes", Chemical Reviews, 2012, pp. 2557-2590, vol. 112.

Claude Y. Legault et al., "Iridium Catalyzed Enantioselective Hydrogenation of N-Iminopyridinium Ylides: Mechanistic Insights", Heterocycles, 2008, pp. 1271-1283, vol. 76, No. 2.

Ying-Guang Zhu et al., "Practical and Scalable Synthesis of Ethyl(R)-Piperidine-3-Acetate", Synthetic Communications: An International Journal for Rapid Communication of Synthetic Organic Chemistry, 2012, pp. 1137-1145, vol. 42.

Zhi-Shi Ye et al., "Iridium-Catalyzed Asymmetric Hydrogenation of Pyridinium Salts", Angewandte Chemie, International Edition 2012, pp. 1-5, vol. 51.

* cited by examiner

METHOD FOR PRODUCING OPTICALLY ACTIVE 2-ARYLPIPERIDINIUM SALT

TECHNICAL FIELD

The present invention relates to a method for producing an optically active 2-arylpiperidinium salt. More specifically, the present invention relates to a method for producing an optically active 2-arylpiperidinium salt, which is useful as pharmaceuticals, agricultural chemicals, flavors, fragrances, synthetic intermediates thereof, and the like.

BACKGROUND ART

Since substituted piperidine derivatives having optical activity are useful as pharmaceuticals, agricultural chemicals, flavors, fragrance, synthetic intermediates thereof, and the like, there is a demand for production of piperidines having high optical activity.

In general, it is necessary to carry out hydrogenation to the corresponding piperidine by using an achiral palladium catalyst or the like (Heterogeneous Catalysis for the Synthetic Chemist, 1996, chapter 17, 421-424, Japanese Patent Application Publication No. 07-242630, and European Patent No. 350733 (pages 65 and 66)) and further to carry out purification by optical resolution. This means that the other optically active isomer is removed as the by-product, and such loss of the product is also disadvantageous in addition to the costs associated with the purification.

Chem. Rev., 2012, 112, 2557-2590 describes asymmetric hydrogenation of nitrogen-containing heterocyclic compounds (including quinoline rings, quinoxaline rings, isoquinoline rings, and the like) other than pyridine rings. However, as described on page 2573, only a few technologies are known for synthesizing a piperidine derivative by asymmetric hydrogenation reaction of a pyridine derivative. As described on page 2574, known technologies for producing an optically active piperidine derivative include (1) asymmetric hydrogenation using a rhodium catalyst; (2) asymmetric hydrogenation using an iridium catalyst; (3) asymmetric hydrogen transfer reaction using an asymmetric Brønsted acid; and the like.

(1) In the asymmetric hydrogenation using a rhodium catalyst, the optical activity is low, or for a high optical purity, multi-step reaction (enamine, substitutution step, and hydrogenation) is necessary.

(2) The asymmetric hydrogenation using an iridium catalyst includes a method of asymmetrically hydrogenating an N-iminopyridinium ylide by using an iridium catalyst as described in Heterocycles, 2008, 76, 1271-1283, and a method for asymmetrically hydrogenating an N-benzylpyridinium ylide by using an iridium catalyst as described in Synthetic Communications: An International Journal for Rapid Communication of Synthetic Organic Chemistry, 2012, 42, 1137-1145 and Angewandte Chemie, International Edition 2012, 51, 1-5. However, it cannnot be said that these conventional technologies are highly versatile production methods, because a step of eliminatiing a protective group at the 1(N)-position is necessary for obtaining a 1-unsubstituted piperidine derivative from a 1-substituted piperidine derivative.

(3) In the asymmetric hydrogen transfer reaction using an asymmetric Brønsted acid described on page 2575 of Chem. Rev., 2012, 112, 2557-2590, Hantzsch ester is used as the hydrogen source. The Hantzsch ester is contained in excess (4 equivalents), and hence has to be separated in purification.

As described above, there is still no simple method which makes it possible to industrially produce an optically active piperidine derivative in a high yield with a high optical purity. In other words, it is difficult to directly obtain an optically active piperidine derivative in a high yield with a high enantiomeric excess by direct asymmetric hydrogenation reaction of a 2-arylpiperidine derivative.

SUMMARY OF INVENTION

An object of the present invention is to provide a method for directly obtaining an optically active 2-arylpiperidinium salt in a high yield with a high enantiomeric excess by direct asymmetric hydrogenation reaction of a 2-arylpiperidinium salt.

The present inventors have earnestly studied production and development of an optically active 2-arylpiperidinium salt by asymmetric hydrogenation reaction of a pyridine ring using an optically active iridium catalyst. As a result, the present inventors have found that asymmetric induction can be achieved in a high yield by asymmetric hydrogenation reaction of a 2-arylpyridinium salt using an iridium complex represented by general formula (3) or general formula (4). This finding has led to the completion of the present invention.

Specifically, the present invention includes the following contents [1] to [5].

[1] A method for producing an optically active 2-arylpiperidinium salt, the method comprising asymmetrically hydrogenating a pyridinium salt in the presence of an iridium complex and hydrogen, the optically active 2-arylpiperidinium salt being represented by the following general formula (1):

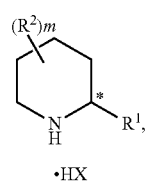

(1)

wherein $R^1$ represents an optionally substituted aryl group having 6 to 20 carbon atoms or an optionally substituted heteroaryl group having 3 to 20 carbon atoms; $R^2$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms; HX represents an acid; * represents an asymmetric carbon atom; and m represents an integer of 1 to 4, provided that $R^2$ is not bonded at the 2-position, the pyridinium salt being represented by the following general formula (2):

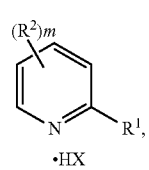

(2)

wherein R[1] represents an optionally substituted aryl group having 6 to 20 carbon atoms or an optionally substituted heteroaryl group having 3 to 20 carbon atoms; R[2] represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms; HX represents an acid; and m represents an integer of 1 to 4, and the iridium complex being represented by the following general formula (3):

IrH(Z)(Q)(PP*)　　　(3), wherein Z represents a halogen atom, PP* represents an optically active bisphosphine, and Q represents a carboxyl group, or the following general formula (4):

[{IrH(PP*)}$_2$(μ-Z)$_3$]Z　　　(4), wherein Z represents a halogen atom and PP* represents an optically active bisphosphine.

[2] The production method according to [1], wherein the optically active bisphosphine is represented by the following general formula (5):

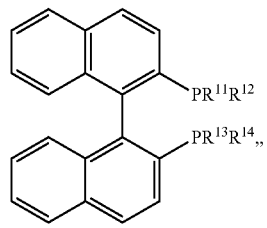

(5)

wherein R[11], R[12], R[13], and R[14] each independently represent a phenyl group optionally substituted with one or more substituents selected from alkyl groups and alkoxy groups, or the following general formula (6):

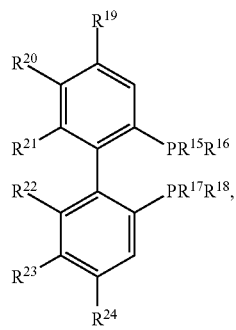

(6)

wherein R[15], R[16], R[17], and R[18] each independently represent a phenyl group optionally substituted with one or more substituents selected from alkyl groups and alkoxy groups; R[19], R[20], R[21], R[22], R[23], and R[24], which may be the same or different, each represent a hydrogen atom, an alkyl group, an alkoxy group, an acyloxy group, a halogen atom, a haloalkyl group, or a dialkylamino group; R[20] with R[21] and R[22] with R[23] may form an optionally substituted methylene chain or an optionally substituted (poly) methylenedioxy group; and R[21] with R[22] may form an optionally substituted methylene chain or an optionally substituted (poly)methylenedioxy group, provided that neither R[21] nor R[22] is a hydrogen atom.

[3] The production method according to [1] or [2], wherein the optically active bisphosphine of the iridium complex represented by general formula (3) is an optically active DTBM-SEGPHOS, and the optically active bisphosphine of the iridium complex represented by general formula (4) is an optically active DIFLUORPHOS.

[4] The production method according to any one of [1] to [3], wherein
the iridium complex is the complex represented by general formula (3).

[5] The production method according to any one of [1] to [4], wherein
the HX is hydrogen bromide or hydrogen iodide.

The asymmetric hydrogenation reaction using the iridium complex specified in the present invention as a catalyst makes it possible to obtain 2-arylpiperidine derivatives highly stereoselectively in high yields. These optically active compounds are useful as synthetic intermediates of various compounds.

DESCRIPTION OF EMBODIMENTS

Hereinafter, the present invention is described.

A method for producing an optically active 2-arylpiperidinium salt of the present invention comprises asymmetrically hydrogenating a pyridinium salt in the presence of an iridium complex and hydrogen, the optically active 2-arylpiperidinium salt being represented by the following general formula (1):

(1)

wherein R[1] represents an optionally substituted aryl group having 6 to 20 carbon atoms or an optionally substituted heteroaryl group having 3 to 20 carbon atoms; R[2] represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms; HX represents an acid; * represents an asymmetric carbon atom; and m represents an integer of 1 to 4, provided that R[2] is not bonded at the 2-position, the pyridinium salt being represented by the following general formula (2):

(2)

wherein $R^1$ represents an optionally substituted aryl group having 6 to 20 carbon atoms or an optionally substituted heteroaryl group having 3 to 20 carbon atoms; $R^2$ represents a hydrogen atom, an optionally substituted alkyl group having 1 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms; HX represents an acid; and m represents an integer of 1 to 4, and the iridium complex being represented by the following general formula (3):

IrH(Z)(Q)(PP*)  (3), wherein Z represents a halogen atom, PP* represents an optically active bisphosphine, and Q represents a carboxyl group, or the following general formula (4):

[{IrH(PP*)}$_2$(μ-Z)$_3$]Z  (4), wherein Z represents a halogen atom and PP* represents an optically active bisphosphine.

Specifically, the aryl group having 6 to 20 carbon atoms as $R^1$ or $R^2$ in general formula (2) include a phenyl group, a naphthyl group, an anthryl group, a phenanthryl group, a biphenyl group, and the like. The aryl group is optionally substituted. The substituents include alkyl groups, alkoxy groups, halogenated alkyl groups, dialkylamino groups, alkylenedioxy groups, and the like. Specific examples of the alkyl group include linear, branched, or cyclic alkyl groups having 1 to 10 carbon atoms, such as a methyl group, an ethyl group, an isopropyl group, a tert-butyl group, and a cyclohexyl group. Specific examples of the alkoxy groups include linear, branched, or cyclic alkoxy groups having 1 to 10 carbon atoms, such as a methoxy group, an ethoxy group, an isopropoxy group, a tert-butoxy group, and a cyclohexyloxy group. Examples of the halogenated alkyl groups include linear or branched halogenated alkyl groups having 1 to 10 carbon atoms. Perfluoroalkyl groups are preferable, and examples thereof include a trifluoromethyl group, a pentafluoroethyl group, and the like. Examples of the dialkylamino groups include dialkylamino groups whose alkyl groups are linear or branched alkyl groups having 1 to 10 carbon atoms, and examples thereof include dialkylamino groups such as a dimethylamino group and a diethylamino group. Examples of the alkylenedioxy groups include alkylenedioxy groups whose alkylene groups are alkylene groups having 1 to 10 carbon atoms, and examples thereof include a methylenedioxy group, an ethylenedioxy group, an isopropylidenedioxy group, and the like.

The heteroaryl group having 3 to 20 carbon atoms as $R^1$ or $R^2$ in general formula (2) specifically includes a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, and the like. The heteroaryl group is optionally substituted. The substituents include the same alkyl groups, alkoxy groups, halogenated alkyl groups, dialkylamino groups, alkylenedioxy groups as those described for the aryl group above, and the like.

The alkyl group having 1 to 20 carbon atoms as $R^2$ in general formula (2) includes linear or branched alkyl groups preferably having 1 to 15 carbon atoms, more preferably having 1 to 10 carbon atoms, and even more preferably having 1 to 6 carbon atoms. Specifically, the alkyl groups include a methyl group, an ethyl group, a n-propyl group, an isopropyl group, a n-butyl group, a sec-butyl group, an isobutyl group, a tert-butyl group, a n-pentyl group, a 2-pentyl group, a tert-pentyl group, a 2-methylbutyl group, a 3-methylbutyl group, a 2,2-dimethylpropyl group, a n-hexyl group, a 2-hexyl group, a 3-hexyl group, a 2-methylpentyl group, a 3-methylpentyl group, a 4-methylpentyl group, and a 2-methylpentan-3-yl group. The alkyl group is optionally substituted. The substituents include the same alkoxy groups, halogenated alkyl groups, dialkylamino groups, alkylenedioxy groups as those described for the aryl group above, and the like.

The cycloalkyl group having 3 to 20 carbon atoms as $R^2$ in general formula (2) specifically includes a cyclopropyl group, a cyclobutyl group, a cyclopentyl group, a cyclohexyl group, a methylcyclopentyl group, a methylcyclohexyl group, and the like. The cycloalkyl group is optionally substituted. The substituents include the same alkyl groups, alkoxy groups, halogenated alkyl groups, dialkylamino groups, alkylenedioxy groups as those described for the aryl group above, and the like.

The alkenyl group having 2 to 20 carbon atoms as $R^2$ in general formula (2) include linear or branched alkenyl groups having 2 to 20 carbon atoms, preferably having 2 to 10 carbon atoms, and more preferably having 2 to 6 carbon atoms. Specifically, the alkenyl groups include an ethenyl group, a n-propenyl group, an isopropenyl group, a 1-butenyl group, a 1-buten-2-yl group, a pentenyl group, a hexenyl group, and the like. The alkenyl group is optionally substituted. The substituents include the same alkyl groups, alkoxy groups, halogenated alkyl groups, dialkylamino groups, alkylenedioxy groups as those described for the aryl group above, and the like.

The aralkyl group having 7 to 20 carbon atoms as $R^2$ in general formula (2) include aralkyl groups having 7 to 20 carbon atoms, preferably having 7 to 15 carbon atoms, and having 7 to 10 carbon atoms in each of which an alkyl group having 1 to 15 carbon atoms is bonded to a monocyclic, polycyclic, or fused-cyclic aryl group having 6 to 20 carbon atoms and preferably having 6 to 14 carbon atoms. Examples thereof include a benzyl group, an α-methylbenzyl group, an α,α-dimethylbenzyl group, a 2-phenylethyl group, a 3-phenylpropyl group, and the like. The aralkyl group is optionally substituted. The substituents include the same alkyl groups, alkoxy groups, halogenated alkyl groups, dialkylamino groups, alkylenedioxy groups as those described for the aryl group above, and the like.

In general formula (2), m represents an integer of 1 to 4 and preferably 1 to 2.

Examples of the acid (HX) forming the salt with the 2-arylpyridine include inorganic acids such as hydrogen fluoride, hydrogen chloride, hydrogen bromide, hydrogen iodide, sulfuric acid, nitric acid, phosphoric acid, and boric acid; carboxylic acids such as formic acid, acetic acid, propionic acid, butyric acid, pivalic acid, chloroacetic acid, trichloroacetic acid, trifluoroacetic acid, oxalic acid, L-tartaric acid, D-tartaric acid, and mandelic acid; and sulfonic acids such as methanesulfonic acid, trifluoromethanesulfonic acid, benzenesulfonic acid, p-toluenesulfonic acid, and camphorsulfonic acid. Preferred are hydrogen chloride, hydrogen bromide, sulfuric acid, acetic acid, pivalic acid, oxalic acid, L-tartaric acid, D-tartaric acid, mandelic acid, methanesulfonic acid, p-toluenesulfonic acid, and camphorsulfonic acid, and more preferred are hydrogen bromide and hydrogen iodide.

The asymmetric hydrogenation is carried out by dissolving a pyridinium salt made from the 2-arylpyridine represented by general formula (2) and the acid (HX) in a solvent which does not inhibit the asymmetric hydrogenation reaction, and adding an iridium catalyst thereto.

Examples of the solvent include alcohol solvents such as methanol, ethanol, and isopropanol; solvents such as dioxane, tetrahydrofuran, diethyl ether, methylene chloride, acetone, ethyl acetate, benzene, toluene, N,N-dimethylformamide, and acetonitrile; mixture solvents thereof; and the like. The iridium catalyst is used in an amount of preferably 1/10 to 1/10,000 molar equivalents and more preferably approximately 1/50 to 1/3,000 molar equivalents relative to the pyridinium salt. The hydrogen pressure in the asymmetric hydrogenation reaction is preferably approximately 1 to 15 MPa, and more preferably approximately 3 to 10 MPa. The temperature in the asymmetric hydrogenation reaction is preferably approximately −20 to 120° C., and more preferably approximately 20 to 100° C. The asymmetric hydrogenation reaction is carried out for preferably approximately 5 to 30 hours, and more preferably approximately 10 to 20 hours.

Note that, in the present invention, it is possible to conduct the asymmetric hydrogenation of the pyridinium salt, without synthesizing the iridium complex in advance. Specifically, the iridium complex represented by general formula (3) is formed in situ by adding an optically active bisphosphine represented by general formula (5) or general formula (6) and an iridium precursor, and the pyridinium salt simultaneously added therewith is asymmetrically hydrogenated.

After the asymmetric hydrogenation, the resultant reaction mixture can be post treated by, for example, removing the catalyst by filtration. After that, for example, another post treatment can be conducted in which the dissolved catalyst is removed by distilling, under reduced pressure, the piperidine derivative produced by a base treatment, if appropriate. The removed catalyst can be reused.

In addition, it is also possible to obtain an optically active 2-arylpiperidine derivative having a higher chemical purity as follows. Specifically, the optically active 2-arylpiperidinium salt is further treated with a base such as an alkali metal hydroxide to liberate the optically active 2-arylpiperidine derivative, and then operations such as extraction and concentration are conducted.

The thus obtained target product has a purity sufficient for the use in a subsequent process. However, the purity may be increased by usual purification techniques such as crystallization, fractional distillation, and column chromatography for further increasing the yield in the subsequent process or the purity of the compound obtained in the subsequent process. Alternatively, the chemical purity or the optical purity may be increased by forming a salt from the optically active 2-arylpiperidine derivative and an acid, and crystallizing the salt from a solvent.

The halogen atom represented by Z in general formula (3) includes a chlorine atom, a bromine atom, an iodine atom, and the like. Z is preferably a chlorine atom or a bromine atom.

Examples of the optically active bisphosphine represented by PP* in general formula (3) include optically active bisphosphines represented by the following general formula (7):

$$R^{P1}R^{P2}P-Q^1-PR^{P3}R^{P4} \qquad (7)$$

wherein $R^{P1}$, $R^{P2}$, $R^{P3}$, and $R^{P4}$ each independently represent an alkyl group, an aryl group, or a heterocyclic group, and $Q^1$ represents an optically active divalent group.

The alkyl group as $R^{P1}$, $R^{P2}$, $R^{P3}$, or $R^{P4}$ of the bisphosphine represented by general formula (7) may be linear, branched, or cyclic, and examples thereof include alkyl groups having 1 to 15 carbon atoms, preferably having 1 to 10 carbon atoms, and more preferably having 1 to 6 carbon atoms. Specific examples thereof include a methyl group, an ethyl group, a n-propyl group, an isopropyl group, a n-butyl group, a sec-butyl group, an isobutyl group, a tert-butyl group, a n-pentyl group, a 2-pentyl group, a tert-pentyl group, a 2-methylbutyl group, a 3-methylbutyl group, a 2,2-dimethylpropyl group, a n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, a cyclohexyl group, a methylcyclopentyl group, a methylcyclohexyl group, and the like.

Meanwhile, examples of the aryl group as $R^{P1}$, $R^{P2}$, $R^{P3}$, or $R^{P4}$ in the bisphosphine represented by general formula (7) include aryl groups having 6 to 14 carbon atoms, and specific examples thereof include a phenyl group, a naphthyl group, an anthryl group, a phenanthryl group, a biphenyl group, and the like. These aryl groups are optionally substituted. Here, the substituents include alkyl groups, alkoxy groups, halogenated alkyl groups, dialkylamino groups, alkylenedioxy groups, and the like. Specific examples of the alkyl groups include linear, branched, or cyclic alkyl groups having 1 to 10 carbon atoms such as a methyl group, an ethyl group, an isopropyl group, a tert-butyl group, and a cyclohexyl group. Meanwhile, examples of the alkoxy groups include linear, branched, or cyclic alkoxy groups having 1 to 10 carbon atoms such as a methoxy group, an ethoxy group, an isopropoxy group, a tert-butoxy group, and a cyclohexyloxy group. Examples of the halogenated alkyl groups include linear or branched halogenated alkyl groups having 1 to 10 carbon atoms, and perfluoroalkyl groups are preferable. Examples thereof include a trifluoromethyl group, a pentafluoroethyl group, and the like. Examples of the dialkylamino groups include dialkylamino groups whose alkyl groups are linear or branched alkyl groups having 1 to 10 carbon atoms, and examples thereof include dialkylamino groups such as a dimethylamino group and a diethylamino group. Examples of the alkylenedioxy groups include alkylenedioxy groups whose alkylene groups are alkylene groups having 1 to 10 carbon atoms, and examples thereof include a methylenedioxy group, an ethylenedioxy group, an isopropylidenedioxy group, and the like.

Meanwhile, the heterocyclic group as $R^{P1}$, $R^{P2}$, $R^{P3}$, or $R^{P4}$ in the bisphosphine represented by general formula (7) includes aliphatic or aromatic heterocyclic groups. Examples of the aliphatic heterocyclic groups include monocyclic aliphatic heterocyclic group (which are preferably 5- to 8-membered, and more preferably 5- or 6-membered) and polycyclic or fused-cyclic aliphatic heterocyclic groups (which are preferably 5- to 8-membered, and more preferably 5- or 6-membered) each of which has 2 to 14 carbon atoms and contains at least one heteroatom (for example, a nitrogen atom, an oxygen atom, a sulfur atom, or the like) as the heteroatom. Specific examples of the aliphatic heterocyclic groups include a pyrrolidyl-2-one group, a piperidino group, a piperazinyl group, a morpholino group, a tetrahydrofuryl group, a tetrahydropyranyl group, a tetrahydrothienyl group, and the like. Examples of the aromatic heterocyclic groups include monocyclic heteroaryl groups (which are preferably 5- to 8-membered and more preferably 5 or 6-membered) and polycyclic or fused-cyclic heteroaryl groups (which are preferably 5- to 14-membered, more preferably 5- or 6-membered) each of which has 2 to 15 carbon atoms and contains at least one heteroatom (for example, a nitrogen atom, an oxygen atom, a sulfur atom, or the like) as the heteroatom. Specific examples of the aromatic heterocyclic groups include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, and the like.

Meanwhile, the divalent group as $Q^1$ in the bisphosphine represented by general formula (7) includes alkylene groups, phenylene groups, biphenyldiyl groups, binaphthalenediyl groups, and the like. Examples of the alkylene groups include alkylene groups having 1 to 6 carbon atoms, and specific examples thereof include a methylene group, an ethylene group, a trimethylene group, a tetramethylene group, a pentamethylene group, and a hexamethylene group. These alkylene groups are optionally substituted with the above-described linear, branched, or cyclic alkyl groups having 1 to 10 carbon atoms such as a methyl group, an ethyl group, an isopropyl group, a tert-butyl group, and a cyclohexyl group, the above-described aryl groups having 6 to 14 carbon atoms such as a phenyl group and a naphthyl group, or the above-described 5- or 6-membered heterocyclic groups such as a piperidino group, a morpholino group, a furyl group, and a pyridyl group. The phenylene groups include o-, m-, or p-phenylene groups, and the phenylene groups are optionally substituted with the above-described linear, branched, or cyclic alkyl groups having 1 to 10 carbon atoms such as a methyl group, an ethyl group, an isopropyl group, a tert-butyl group, and a cyclohexyl group, the above-described linear, branched, or cyclic alkoxy groups having 1 to 10 carbon atoms such as a methoxy group, an ethoxy group, an isopropoxy group, a tert-butoxy group, and a cyclohexyloxy group; a hydroxy group; an amino group; or dialkylamino groups such as a dimethylamino group and a diethylamino group (the alkyl groups thereof are linear or branched alkyl groups having 1 to 10 carbon atoms); or the like. The biphenyldiyl groups and the binaphthalenediyl groups preferably have a 1,1'-biaryl-2,2'-diyl-type structure, and the biphenyldiyl groups and binaphthalenediyl groups are optionally substituted with the above-described linear, branched, or cyclic alkyl group having 1 to 10 carbon atoms such as a methyl group, an ethyl group, an isopropyl group, a tert-butyl group, and a cyclohexyl group; the above-described alkoxy groups having 1 to 10 carbon atoms such as a methoxy group, an ethoxy group, an isopropoxy group, a tert-butoxy group, and a cyclohexyloxy group; acyloxy groups having 2 to 20 carbon atoms such as an acetoxy group, a propanoyloxy group, and a benzoyloxy group; halogen atoms such as a chlorine atom, a bromine atom, and a fluorine atom; haloalkyl groups having 1 to 10 carbon atoms such as a trifluoromethyl group and a pentafluoroethyl group; a hydroxy group; an amino group; dialkylamino groups such as a dimethylamino group and a diethylamino group (the alkyl groups thereof are linear or branched alkyl groups having 1 to 10 carbon atoms): or the like.

Examples of the optically active bisphosphine represented by general formula (7) includes optically active bisphosphines known prior to the filing of this application, and preferred one of the known optically active bisphosphines is an optically active bisphosphine represented by general formula (5):

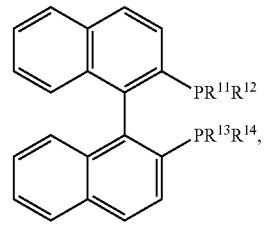

(5)

wherein $R^{11}$, $R^{12}$, $R^{13}$, and $R^{14}$ each independently represent a phenyl group optionally substituted with one or more substituents selected from alkyl groups and alkoxy groups.

Examples of the alkyl group as $R^{11}$, $R^{12}$, $R^{13}$, or $R^{14}$ in the optically active bisphosphine represented by general formula (5) include linear, branched, or cyclic alkyl groups having 1 to 10 carbon atoms such as a methyl group, an ethyl group, an isopropyl group, a tert-butyl group, and a cyclohexyl group. Meanwhile, examples of the alkoxy group as $R^{11}$, $R^{12}$, $R^{13}$, or $R^{14}$ in the optically active bisphosphine represented by general formula (5) include linear, branched, or cyclic alkoxy groups having 1 to 10 carbon atoms such as a methoxy group, an ethoxy group, an isopropoxy group, a tert-butoxy group, and a cyclohexyloxy group.

Specific examples of the optically active bisphosphine represented by general formula (5) include 2,2'-bis-(diphenylphosphino)-1,1'-binaphthyl (hereinafter referred to as BINAP (registered trademark)), 2,2'-bis-(di-p-tolylphosphino)-1,1'-binaphthyl (hereinafter referred to as Tol-BINAP), 2,2'-bis-(di-m-tolylphosphino)-1,1'-binaphthyl, 2,2'-bis(di-3,5-xylylphosphino)-1,1'-binaphthyl (hereinafter referred to as DM-BINAP), 2,2'-bis(di-p-tert-butylphenylphosphino)-1,1'-binaphthyl, 2,2'-bis(di-p-methoxyphenylphosphino)-1,1'-binaphthyl, 2,2'-bis(di-p-chlorophenylphosphino)-1,1'-binaphthyl, 2,2'-bis(dicyclopentylphosphino)-1,1'-binaphthyl (Cp-BINAP), 2,2'-bis(dicyclohexylphosphino)-1,1'-binaphthyl (Cy-BINAP), and the like.

Another optically active bisphosphine preferably used in the present invention is an optically active bisphosphine represented by the following general formula (6):

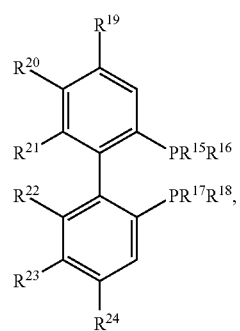

(6)

wherein $R^{15}$, $R^{16}$, $R^{17}$, and $R^{18}$ each independently represent a phenyl group optionally substituted with one or more substituents selected from alkyl groups and alkoxy groups; $R^{19}$, $R^{20}$, $R^{21}$, $R^{22}$, $R^{23}$, and $R^{24}$, which may be the same or different, each represent a hydrogen atom, an alkyl group, an alkoxy group, an acyloxy group, a halogen atom, a haloalkyl group, or a dialkylamino group; $R^{20}$ with $R^{21}$ and $R^{22}$ with $R^{23}$ may form an optionally substituted methylene chain or an optionally substituted (poly) methylenedioxy group; and $R^{21}$ with $R^{22}$ may form an optionally substituted methylene chain or an optionally substituted (poly)methylenedioxy group, provided that neither $R^{21}$ nor $R^{22}$ is a hydrogen atom.

Examples of the alkyl group as $R^{15}$, $R^{16}$, $R^{17}$, or $R^{18}$ in the optically active bisphosphine represented by general formula (6) include linear, branched, or cyclic alkyl group having 1 to 10 carbon atoms such as a methyl group, an ethyl group, an isopropyl group, a tert-butyl group, and a cyclohexyl group. Meanwhile, examples of the alkoxy group as $R^{15}$, $R^{16}$, $R^{17}$, or $R^{18}$ in the optically active bisphosphine represented by general formula (6) include linear, branched, or cyclic alkoxy groups having 1 to 10 carbon atoms such as a methoxy group, an ethoxy group, an isopropoxy group, a tert-butoxy group, and a cyclohexyloxy group.

The alkyl group and the alkoxy group as $R^{19}$, $R^{20}$, $R^{21}$, $R^{22}$, $R^{23}$, or $R^{24}$ in the optically active bisphosphine represented by general formula (6) have the same meanings as the alkyl group and the alkoxy group as $R^{11}$, $R^{12}$, $R^{13}$, or $R^{14}$ in the optically active bisphosphine represented by general formula (5). Meanwhile, examples of the acyloxy group as $R^{19}$, $R^{20}$, $R^{21}$, $R^{22}$, $R^{23}$, or $R^{24}$ in the optically active bisphosphine represented by general formula (6) include an acetoxy group, a propanoyloxy group, a trifluoroacetoxy group, a benzoyloxy group, and the like. Examples of the halogen atom as $R^{19}$, $R^{20}$, $R^{21}$, $R^{22}$, $R^{23}$, or $R^{24}$ include a chlorine atom, a bromine atom, a fluorine atom, and the like. Examples of the haloalkyl group as $R^{19}$, $R^{20}$, $R^{21}$, $R^{22}$, $R^{23}$, or $R^{24}$ include haloalkyl groups having 1 to 4 carbon atoms such as a trifluoromethyl group. Examples of the dialkylamino group as $R^{19}$, $R^{20}$, $R^{21}$, $R^{22}$, $R^{23}$, or $R^{24}$ include a dimethylamino group, a diethylamino group, and the like.

The methylene chain which may be formed by $R^{20}$ with $R^{21}$ or $R^{22}$ with $R^{23}$ in the optically active bisphosphine represented by general formula (6) is preferably a methylene chain having 3 to 5 carbon atoms, and specifically includes a trimethylene group, a tetramethylene group, and a pentamethylene group. In addition, substituents which may be possessed by the methylene chain include alkyl groups, halogen atoms, and the like, and specific examples of these alkyl groups and halogen atoms include the above-described alkyl groups having 1 to 6 carbon atoms, fluorine atoms, and the like. Meanwhile, the methylene chain of the (poly)methylenedioxy group which may be formed by $R^{20}$ with $R^{21}$ or $R^{22}$ with $R^{23}$ in the optically active bisphosphine represented by general formula (6) is preferably a methylene chain having 1 to 3 carbon atoms, and specifically includes a methylene group, an ethylene group, and a trimethylene group. In addition, substituents which may be possessed by the (poly)methylenedioxy group include alkyl groups, halogen atoms, and the like, and specific examples of these alkyl groups and halogen atoms include the above-described alkyl groups having 1 to 6 carbon atoms, fluorine atoms, and the like.

The methylene chain which may be formed by $R^{21}$ and $R^{22}$ in the optically active bisphosphine represented by general formula (6) is preferably a methylene chain having 3 to 5 carbon atoms, and specifically includes a trimethylene group, a tetramethylene group, and a pentamethylene group. In addition, substituents which may be possessed by the methylene chain include alkyl groups, halogen atoms, and the like, and specific examples of these alkyl groups and halogen atoms include the above-described alkyl groups having 1 to 6 carbon atoms, fluorine atoms, and the like. Meanwhile, the methylene chain of the (poly)methylenedioxy group which may be formed by $R^{20}$ with $R^{21}$ or $R^{22}$ with $R^{23}$ in the optically active bisphosphine represented by general formula (6) is preferably a methylene chain having 1 to 3 carbon atoms, and specifically includes a methylene group, an ethylene group, and a trimethylene group. In addition, substituents which may be possessed by the (poly)methylenedioxy group include alkyl groups, halogen atoms, and the like, and specific examples of these alkyl groups and halogen atoms include the above-described alkyl groups having 1 to 6 carbon atoms, fluorine atoms, and the like.

Specific examples of the optically active bisphosphine represented by general formula (6) include
2,2'-bis(diphenylphosphino)-5,5',6,6',7,7',8,8'-octahydro-1,1'-binaphthyl (hereinafter referred to as $H_8$-BINAP),
2,2'-bis(di-p-tolylphosphino)-5,5',6,6',7,7',8,8'-octahydro-1,1'-binaphthyl,
2,2'-bis(di-m-tolylphosphino)-5,5',6,6',7,7',8,8'-octahydro-1,1'-binaphthyl,
2,2'-bis(di-3,5-xylylphosphino)-5,5',6,6',7,7',8,8'-octahydro-1,1'-binaphthyl,
2,2'-bis(di-p-tert-butylphenylphosphino)-5,5',6,6',7,7',8,8'-octahydro-1,1'-binaphthyl,
2,2'-bis(di-p-methoxyphenylphosphino)-5,5',6,6',7,7',8,8'-octahydro-1,1'-binaphthyl,
2,2'-bis(di-p-chlorophenylphosphino)-5,5',6,6',7,7',8,8'-octahydro-1,1'-binaphthyl,
2,2'-bis(dicyclopentylphosphino)-5,5',6,6',7,7',8,8'-octahydro-1,1'-binaphthyl,
2,2'-bis(dicyclohexylphosphino)-5,5',6,6',7,7',8,8'-octahydro-1,1'-binaphthyl,
(4,4'-bi-1,3-benzodioxole)-5,5'-diyl)bis(diphenylphosphine) (SEGPHOS),
(4,4'-bi-1,3-benzodioxole)-5,5'-diyl)bis(bis(3,5-xylyl)phosphine (DM-SEGPHOS),
(4,4'-bi-1,3-benzodioxole)-5,5'-diyl)bis(bis(3,5-di-t-butyl-4-methoxyphenyl)phosphine (DTBM-SEGPHOS),
(4,4'-bi-1,3-benzodioxole)-5,5'-diyl)bis(bis(4-methoxyphenyl)phosphine,
(4,4'-bi-1,3-benzodioxole)-5,5'-diyl)bis(dicyclohexylphosphine (Cy-SEGPHOS),
(4,4'-bi-1,3-benzodioxole)-5,5'-diyl)bis(bis(3,5-di-t-butyl phenyl)phosphine,
4,4'-bi(2,2-difluoro-1,3-benzodioxole)-5,5'-diyl)bis(diphenylphosphine) (DIFLUORPHOS),
2,2'-bis(diphenylphosphino)-4,4',6,6'-tetramethyl-5,5'-dimethoxy-1,1'-biphenyl,
2,2'-bis(di-p-methoxyphenylphosphino)-4,4',6,6'-tetramethyl-5,5'-dimethoxy-1,1'-biphenyl,
2,2'-bis(diphenylphosphino)-4,4',6,6'-tetra(trifluoromethyl)-5,5'-dimethyl-1,1'-biphenyl,
2,2'-bis(diphenylphosphino)-4,6-di(trifluoromethyl)-4',6'-dimethyl-5'-methoxy-1,1'-biphenyl,
2-dicyclohexylphosphino-2'-diphenylphosphino-4,4',6,6'-tetramethyl-5,5'-dimethoxy-1,1'-biphenyl,
2,2'-bis(diphenylphosphino)-6,6'-dimethyl-1,1-biphenyl,
2,2'-bis(diphenylphosphino)-4,4',6,6'-tetramethyl-1,1'-biphenyl,
2,2'-bis(diphenylphosphino)-3,3',6,6'-tetramethyl-1,1'-biphenyl),
2,2'-bis(diphenylphosphino)-4,4'-difluoro-6,6'-dimethyl-1,1'-biphenyl,
2,2'-bis(diphenylphosphino)-4,4'-bis(dimethylamino)-6,6'-dimethyl-1,1'-biphenyl,
2,2'-bis(di-p-tolylphosphino)-6,6'-dimethyl-1,1'-biphenyl,
2,2'-bis(di-o-tolylphosphino)-6,6'-dimethyl-1,1'-biphenyl,
2,2'-bis(di-m-fluorophenylphosphino)-6,6'-dimethyl-1,1'-biphenyl,
1,11-bis(diphenylphosphino)-5,7-dihydrobenzo[c,e]oxepin,
2,2'-bis(diphenylphosphino)-6,6'-dimethoxy-1,1'-biphenyl, 2,2'-bis(diphenylphosphino)-5,5',6,6'-tetramethoxy-1,1'-biphenyl,
2,2'-bis(di-p-tolylphosphino)-6,6'-dimethoxy-1,1'-biphenyl,
2,2'-bis(diphenylphosphino)-4,4',5,5',6,6'-hexamethoxy-1,1'-biphenyl, and the like.

Other usable optically active bisphosphines include N,N-dimethyl-1-[1',2-bis(diphenylphosphino)ferrocenyl]ethyl amine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino)butane, 1,2-bis{(o-methoxyphenyl)phenylphosphino}ethane, 1,2-bis(2,5-dialkylphospholano)benzene, 1,2-bis(2,5-dialkylphospholano)ethane, 1-(2,5-dialkylphospholano)-2-(diphenylphosphino)benzene, 1-(2,5-dialkylphospholano)-2-(di(alkylphenyl)phosphino)benzene, 5,6-bis(diphenylphosphino)-2-norbornene, N,N'-bis(diphenylphosphino)-N,N'-bis(1-phenylethyl)ethylene diamine, 1,2-bis(diphenylphosphino)propane, 2,4-bis(diphenylphosphino)pentane, and the like. Note that, as a matter of course, optically active bisphosphines usable in the present invention are not limited thereto at all.

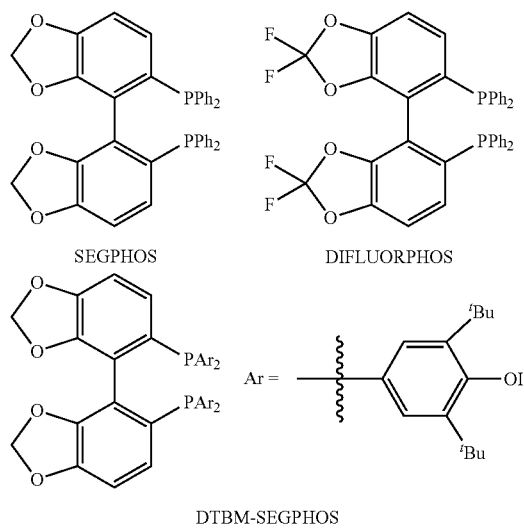

Examples of iridium precursor compounds usable for forming the iridium complex represented by general formula (3) include di-μ-chlorotetrakis(cyclooctene)diiridium ([IrCl(coe)$_2$]$_2$), di-μ-bromotetrakis(cyclooctene)diiridium ([IrBr(coe)$_2$]$_2$), di-μ-iodotetrakis(cyclooctene)diiridium ([IrI(coe)$_2$]$_2$), di-μ-chlorobis(1,5-cyclooctadiene)diiridium ([IrCl(cod)]$_2$), di-μ-bromobis(1,5-cyclooctadiene)diiridium ([IrBr(cod)]$_2$), di-μ-iodobis(1,5-cyclooctadiene)diiridium ([IrI(cod)]$_2$), di-μ-chlorobis(bicyclo[2,2,1]hepta-2,5-diene)diiridium ([IrCl(nbd)]$_2$), di-μ-bromobis(bicyclo[2,2,1]hepta-2,5-diene)diiridium ([IrBr(nbd)]$_2$), di-μ-iodobis(bicyclo[2,2,1]hepta-2,5-diene)diiridium ([IrI(nbd)]$_2$), and the like.

The iridium complex represented by general formula (3) can be prepared by reacting the iridium precursor compound with the optically active bisphosphine represented by general formula (5), (6), or (7), followed by a reaction with a carboxylic acid.

The iridium complex represented by general formula (4) can be synthesized by the method described in International Publication No. WO2006/022020. Specifically, this iridium complex can be prepared by reacting the above-described iridium precursor compound with the optically active bisphosphine represented by general formula (5), (6), or (7), followed by a reaction with a hydrogen halide or a hydrohalic acid. The optically active bisphosphine is used in a substantially equimolar amount to the iridium atoms in the iridium precursor.

EXAMPLES

The present invention is described in detail based on Examples shown below. However, the present invention is not limited to these examples at all. Note that the analytical instruments shown below were used in Examples.
Nuclear magnetic resonance spectroscopy (NMR): MERCURY300-C/H (VARIAN)
Mass spectrometry (MS): LCMS-IT-TOF (Shimadzu Corp.)
Gas chromatography (GC): GC-14A (Shimadzu Corp.)
  GC (chemical purity): capillary HP-1
  Injection temperature: 220° C., Detection temperature: 250° C.
  100° C. (0 min)-10° C./min-250° C. (5 min)
  GC (optical purity): capillary CP-CHIRASIL-DEX-CB
  Injection temperature: 250° C., Detection temperature: 250° C.
  130° C. (30 min)
HPLC (optical purity): column Daisel AD-H
  Column temperature: 30° C., Detection wavelength: 215 nm, Hex/IPA=97/3
(Synthesis of IrHCl(OAc)((R)-DTBM-SEGPHOS))

To a Schlenk tube purged with nitrogen, 100 mg (0.11 mmol) of [IrCl(coe)$_2$]$_2$, 280 mg (0.24 mmol) of (R)-DTBM-SEGPHOS, and 3 ml of toluene were added, and stirred at room temperature for 1 hour. Subsequently, 138 μl (2.4 mmol) of acetic acid was added. After stirring for 2 hours, the reaction liquid was concentrated. Thus, 316 mg of the title complex was obtained. Yield: 96%.
$^1$H NMR (CD$_2$Cl$_2$): δ −26.8 (t, J=21.4 Hz, 1H), 1.31 (s, 36H), 1.32 (s, 9H), 1.34 (s, 9H), 1.35 (s, 36H), 1.37 (s, 9H), 2.33 (s, 3H), 3.61 (s, 3H), 3.63 (s, 3H), 3.69 (s, 3H), 3.70 (s, 3H), 5.62 (m, 4H), 6.24 (dd, J=8.2, 12.1 Hz, 1H), 6.34 (dd, J=1.1, 8.2 Hz, 1H), 6.54 (dd, J=1.1, 8.2 Hz, 1H), 6.84 (dd, J=8.2, 11.9 Hz, 1H), 7.09-7.39 (m, 8H)
$^{31}$P NMR (CD$_2$Cl$_2$): δ −0.55 (br), −4.98 (br)
HRMS (ESI): m/z calced for C$_{76}$H$_{104}$O$_{10}$P$_2$ClIr [M-H]+ 1465.6339; m/z found 1465.6289
(Synthesis of IrHCl(CF$_3$CO$_2$)((R)-DTBM-SEGPHOS))

To a Schlenk tube purged with nitrogen, 100 mg (0.11 mmol) of [IrCl(coe)$_2$]$_2$, 280 mg (0.24 mmol) of (R)-DTBM-SEGPHOS, and 3 ml of toluene were added, and stirred at room temperature for 1 hour. Subsequently, 138 μl (2.4 mmol) of trifluoroacetic acid was added. After stirring for 2 hours, the reaction liquid was concentrated. Thus, 328 mg of the title complex was obtained. Yield: 98%.
$^{31}$P NMR(C$_6$D$_6$): δ −0.88 (br), −4.62 (br)
(Synthesis of IrHCl(C$_6$H$_5$CO$_2$)((R)-DTBM-SEGPHOS))

To a Schlenk tube purged with nitrogen, 100 mg (0.11 mmol) of [IrCl(coe)$_2$]$_2$, 280 mg (0.24 mmol) of (R)-DTBM-SEGPHOS, and 3 ml of toluene were added, and stirred at room temperature for 1 hour. Subsequently, 130 mg (0.96 mmol) of benzoic acid was added. After stirring for 2 hours, the reaction liquid was concentrated. Thus, 323 mg of the title complex was obtained. Yield: 95%.
$^{31}$P NMR (C$_6$D$_6$): δ −1.09 (br), −4.48 (br)
(Synthesis of [{IrH((S)-DIFLUORPHOS)}$_2$(μ-Cl)$_3$]Cl)

To a Schlenk tube purged with nitrogen, 328 mg (0.36 mmol) of [IrCl(coe)$_2$]$_2$, 512 mg (0.72 mmol) of (S)-DIFLUORPHOS, and 3 ml of toluene were added at room temperature for 16 hours. Subsequently, 0.4 ml of concentrated hydrochloric acid was added. After stirring for 2 hours, the reaction liquid was concentrated. The obtained solid was dissolved in a small amount of methylene chloride, and hexane was added thereto. The obtained solid was separated by filtration and dried. Thus, 621 mg of the title complex was obtained. Yield: 90%.
HRMS (ESI): m/z calced for $C_{76}H_{50}O_4P_2Cl_3Ir_2$ [M-Cl]$^+$ 1857.0600; m/z found 1857.0939
(Synthesis of [{IrH((S)-SEGPHOS)}$_2$(μ-Cl)$_3$]Cl)

To a Schlenk tube purged with nitrogen, 311 mg (0.35 mmol) of [IrCl(coe)$_2$]$_2$, 434 mg (0.70 mmol) of (S)-SEGPHOS, and 3 ml of toluene were added, and stirred at room temperature for 16 hours. Subsequently, 0.4 ml of concentrated hydrochloric acid was added. After stirring for 2 hours, the precipitated solid was separated by filtration and dried. Thus, 551 mg of the title complex was obtained. Yield: 90%.

Example 1

Asymmetric Hydrogenation Reaction of 2-Phenylpyridinium Bromide

To a 100 ml stainless steel autoclave, 14.6 mg (0.01 mmol) of IrHCl(OAc)((R)-DTBM-SEGPHOS) and 118 mg (0.5 mmol) of 2-phenylpyridinium bromide were added, and the autoclave was purged with nitrogen. Then, 2.0 ml of tetrahydrofuran was added thereto. Subsequently, hydrogen was introduced at a pressure of 10.0 MPa, followed by stirring at 80° C. for 16 hours. After cooling, the reaction product was analyzed by GC. The conversion was 91%, and the enantiomeric excess was 52% ee.

Example 2

Asymmetric Hydrogenation Reaction of 2-Phenylpyridinium Bromide

To a 100 ml stainless steel autoclave, 7.6 mg (0.005 mmol) of IrHCl(CF$_3$CO$_2$)((R)-DTBM-SEGPHOS) and 118 mg (0.5 mmol) of 2-phenylpyridinium bromide were added, and the autoclave was purged with nitrogen. Then, 2.0 ml of tetrahydrofuran was added thereto. Subsequently, hydrogen was introduced at a pressure of 5.0 MPa, followed by stirring at 80° C. for 16 hours. After cooling, the reaction product was analyzed by GC. The conversion was 53%, and the enantiomeric excess was 56% ee.

Example 3

Asymmetric Hydrogenation Reaction of 2-Phenylpyridinium Bromide

To a 100 ml stainless steel autoclave, 7.7 mg (0.005 mmol) of IrHCl(C$_6$H$_5$CO$_2$)((R)-DTBM-SEGPHOS) and 118 mg (0.5 mmol) of 2-phenylpyridinium bromide were added, and the autoclave was purged with nitrogen. Then, 2.0 ml of tetrahydrofuran was added thereto. Subsequently, hydrogen was introduced at a pressure of 5.0 MPa, followed by stirring at 80° C. for 16 hours. After cooling, the reaction product was analyzed by GC. The conversion was 38%, and the enantiomeric excess was 53% ee.

Example 4

Asymmetric Hydrogenation Reaction of 2-Phenylpyridinium Iodide

To a 100 ml stainless steel autoclave, 14.6 mg (0.01 mmol) of IrHCl(OAc)((R)-DTBM-SEGPHOS) and 141 mg (0.5 mmol) of 2-phenylpyridinium iodide were added, and the autoclave was purged with nitrogen. Then, 2.0 ml of tetrahydrofuran was addeed thereto. Subsequently, hydrogen was introduced at a pressure of 5.0 MPa, followed by stirring at 80° C. for 16 hours. After cooling, the reaction product was analyzed by GC. The conversion was 27%, and the enantiomeric excess was 65% ee.

Example 5

Asymmetric Hydrogenation Reaction of 2-Methyl-6-phenylpyridinium Bromide

To a 100 ml stainless steel autoclave, 23.7 mg (0.0125 mmol) of [{IrH((S)-DIFLUORPHOS)}$_2$(μ-Cl)$_3$]Cl and 63 mg (0.25 mmol) of 2-phenylpyridinium bromide were added, and the autoclave was pruged with argon. Then, 3.0 ml of dioxane was added thereto. Subsequently, hydrogen was introduced at a pressure of 1.0 MPa, followed by stirring at 100° C. for 20 hours. After cooling, the reaction product was analyzed by NMR and HPLC. The conversion was 44%, and the enantiomeric excess was 75% ee.

Example 6

Asymmetric Hydrogenation Reaction of 2-Methyl-6-phenylpyridinium Bromide

To a 100 ml stainless steel autoclave, 21.9 mg (0.0125 mmol) of [{IrH((S)-SEGPHOS)}$_2$(μ-Cl)$_3$]Cl and 63 mg (0.25 mmol) of 2-phenylpyridinium bromide were added, and the autoclave was pruged with argon. Then, 3.0 ml of dioxane was added thereto. Subsequently, hydrogen was introduced at a pressure of 1.0 MPa, followed by stirring at 100° C. for 20 hours. After cooloing, the reaction product was analyzed by NMR and HPLC. The conversion was 91%, and the enantiomeric excess was 67% ee.

The invention claimed is:

1. A method for producing an optically active 2-arylpiperidinium salt, the method comprising asymmetrically hydrogenating a pyridinium salt in the presence of an iridium complex and hydrogen, the optically active 2-arylpiperidinium salt being represented by the following general formula (1):

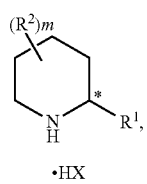

·HX wherein $R^1$ represents an aryl group having 6 to 20 carbon atoms; $R^2$ represents a hydrogen atom or an optionally substituted alkyl group having 1 to 20 carbon atoms; HX represents an acid; * represents an asymmetric carbon atom; and m represents an integer of 1 to 4, provided that $R^2$ is not bonded at the 2-position, the pyridinium salt being represented by the following general formula (2):

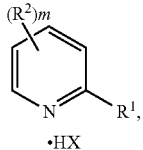

(2)

wherein $R^1$ represents an aryl group having 6 to 20 carbon atoms; $R^2$ represents a hydrogen atom or an optionally substituted alkyl group having 1 to 20 carbon atoms; HX represents an acid; and m represents an integer of 1 to 4, and the iridium complex being represented by the following general formula (3) or general formula (4):

IrH(Z)(Q)(PP*)  (3), wherein Z represents a halogen atom, PP* represents an optically active bisphosphine, and Q represents a carboxyl group;

[{IrH(PP*)}$_2$(μ-Z)$_3$]Z  (4), wherein Z represents a halogen atom and PP* represents an optically active bisphosphine.

2. The production method according to claim 1, wherein the optically active bisphosphine is represented by the following general formula (5):

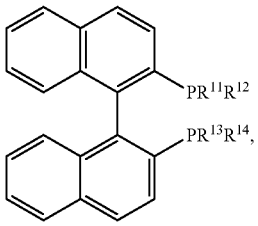

(5)

wherein $R^{11}$, $R^{12}$, $R^{13}$, and $R^{14}$ each independently represent a phenyl group optionally substituted with one or more substituents selected from alkyl groups and alkoxy groups, or the following general formula (6):

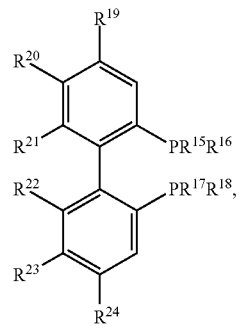

(6)

wherein $R^{15}$, $R^{16}$, $R^{17}$, and $R^{18}$ each independently represent a phenyl group optionally substituted with one or more substituents selected from alkyl groups and alkoxy groups; $R^{19}$, $R^{20}$, $R^{21}$, $R^{22}$, $R^{23}$, and $R^{24}$, which may be the same or different, each represent a hydrogen atom, an alkyl group, an alkoxy group, an acyloxy group, a halogen atom, a haloalkyl group, or a dialkylamino group; $R^{20}$ with $R^{21}$ and $R^{22}$ with $R^{23}$ may form an optionally substituted methylene chain or an optionally substituted (poly) methylenedioxy group; and $R^{21}$ with $R^{22}$ may form an optionally substituted methylene chain or an optionally substituted (poly)methylenedioxy group, provided that neither $R^{21}$ nor $R^{22}$ is a hydrogen atom.

3. The production method according to claim 1, wherein the optically active bisphosphine of the iridium complex represented by general formula (3) is an optically active (4,4'-bi-1,3-benzodioxole)-5,5'-diyl)bis(bis(3,5-di-t-butyl-4-methoxyphen-yl)phosphine (DTBM-SEG-PHOS), and the optically active bisphosphine of the iridium complex represented by general formula (4) is an optically active 4,4'-bi(2,2-difluoro-1,3-benzodioxole)-5,5'-diyl) bis (diphenylphosphine).

4. The production method according to claim 1, wherein the iridium complex is the complex represented by general formula (3).

5. The production method according to claim 1, wherein the HX is hydrogen bromide or hydrogen iodide.

* * * * *